(12) United States Patent
Verschueren et al.

(10) Patent No.: US 9,772,621 B2
(45) Date of Patent: Sep. 26, 2017

(54) METHODS FOR THE MANUFACTURE OF INTRALUMINAL ENDOPROSTHESIS

(71) Applicant: MATERIALISE N.V., Leuven (BE)

(72) Inventors: Peter Verschueren, Bierbeek (BE); Jari Heikki Petteri Pallari, Rovaniemi (FI); Koen Engelborghs, Vaalbeek (BE); Wilfried Vancraen, Huldenberg (BE)

(73) Assignee: MATERIALISE N.V., Leuven (BE)

( * ) Notice: Subject to any disclaimer, the term of this patent is extended or adjusted under 35 U.S.C. 154(b) by 535 days.

(21) Appl. No.: 14/245,985

(22) Filed: Apr. 4, 2014

(65) Prior Publication Data
US 2014/0222184 A1    Aug. 7, 2014

Related U.S. Application Data

(63) Continuation of application No. PCT/EP2012/069715, filed on Oct. 5, 2012.
(Continued)

(30) Foreign Application Priority Data

Oct. 7, 2011   (EP) .................................... 11184365

(51) Int. Cl.
*G06F 19/00*    (2011.01)
*G05B 19/4099*  (2006.01)
(Continued)

(52) U.S. Cl.
CPC ............ *G05B 19/4099* (2013.01); *A61F 2/06* (2013.01); *A61F 2/91* (2013.01); *B29C 33/3835* (2013.01); *B29C 33/448* (2013.01); *G06T 17/10* (2013.01); *G06T 17/20* (2013.01); *A61F 2210/0076* (2013.01); *A61F 2240/004* (2013.01);
(Continued)

(58) Field of Classification Search
CPC ... G05B 19/4099; G06T 17/10; B29C 33/448; A61F 2/06; A61F 2/91
USPC ....... 700/98, 118, 163; 623/1.15, 1.11, 2.17, 623/920
See application file for complete search history.

(56) References Cited

U.S. PATENT DOCUMENTS

| 7,722,663 B1 * | 5/2010 | Austin ...................... A61F 2/07 623/1.22 |
| 2005/0096729 A1 * | 5/2005 | Donadio, III ............. A61F 2/91 623/1.15 |

(Continued)

FOREIGN PATENT DOCUMENTS

| DE | 2537251 A1 | 2/1977 |
| EP | 0770401 A2 | 5/1997 |

(Continued)

OTHER PUBLICATIONS

International Search Report issued for related application PCT/EP2012/069715 on Dec. 19, 2012.

*Primary Examiner* — Mohammad Ali
*Assistant Examiner* — Sheela S Rao

(57) ABSTRACT

The application provides molds for the manufacture of intraluminal endoprostheses and methods for their manufacture. In particular embodiments, the methods comprise the steps of providing a 3D model of the mold, meshing the model, manufacturing a mold based on said meshed 3D model. Also provided herein are methods for manufacturing an endoprosthesis using said mold.

13 Claims, 3 Drawing Sheets

Related U.S. Application Data

(60) Provisional application No. 61/544,349, filed on Oct. 7, 2011.

(51) Int. Cl.
| | |
|---|---|
| *A61F 2/06* | (2013.01) |
| *A61F 2/91* | (2013.01) |
| *B29C 33/38* | (2006.01) |
| *B29C 33/44* | (2006.01) |
| *G06T 17/10* | (2006.01) |
| *G06T 17/20* | (2006.01) |
| B29C 33/48 | (2006.01) |
| B29C 67/00 | (2017.01) |
| B29L 31/00 | (2006.01) |

(52) U.S. Cl.
CPC ... *A61F 2250/0039* (2013.01); *B29C 33/3842* (2013.01); *B29C 33/485* (2013.01); *B29C 67/0051* (2013.01); *B29L 2031/7532* (2013.01)

(56) References Cited

U.S. PATENT DOCUMENTS

| | | | |
|---|---|---|---|
| 2006/0129228 A1* | 6/2006 | Golesworthy | A61B 17/12 623/1.16 |
| 2009/0048659 A1* | 2/2009 | Weber | A61L 27/306 623/1.15 |

FOREIGN PATENT DOCUMENTS

| | | |
|---|---|---|
| GB | 1520258 A | 8/1978 |
| WO | 2004026178 A2 | 4/2004 |

* cited by examiner

METHODS FOR THE MANUFACTURE OF INTRALUMINAL ENDOPROSTHESIS

CROSS-REFERENCE TO RELATED APPLICATIONS

This application is a continuation under 35 U.S.C. §120 of International Application No. PCT/EP2012/069715, filed Oct. 5, 2012 (published by the International Bureau as International Publication No. WO 2013/050525 on Apr. 11, 2013), which claims priority to: (1) U.S. Provisional Patent Application No. 61/544,349, filed Oct. 7, 2011, and (2) European Patent Application No. 11184365.2, filed Oct. 7, 2011. The entire contents of each of the above-referenced applications are hereby incorporated by reference.

BACKGROUND OF THE INVENTION

Field of the Invention

The application provides intraluminal prosthesis, methods for the manufacture of intraluminal endoprostheses and mandrels for the manufacture of such endoprostheses.

Description of the Related Technology

Endoprostheses are a commonly used way of dealing with diseases in interventional medicine and surgery. Mesh-based endoprostheses such as stents, stent grafts, heart valve frames, etc. are of particular importance in cardiovascular applications. Also other fields of medicine make use of such endoprostheses, e.g. pulmonary tract stents, oesophagus stents, etc.

Intraluminal endoprostheses such as stents are typically designed such that they are deployable by catheter or similar stent delivery system, as it is desirable for stent placement procedures to be minimally invasive. Some stents are self-expandable, whereas other stents are inflated via a balloon inside the stent in order to force the stent to open.

Currently, the majority of stents have a cylindrical outer shape, regardless of the anatomy of the lumen in which the stents are to be deployed. Although stents typically are flexible, insertion of a stent which is not optimized to fit the exact patient's anatomy often leads to suboptimal intervention results including localized turbulence in the blood, unnatural stresses on the vessel wall, vessel injury, endoprosthesis breaking, endoprosthesis migration, etc.

U.S. Pat. No. 7,722,663 describes a method for manufacturing a custom, personalized endoprosthesis using a mandrel which is adapted to the actual patient's anatomy. In this method, a V-shape undulated wire, typically in a shape memory or superelastic alloy, is draped around the mandrel, followed by a heat treatment to set the wire onto the mandrel. The wire is then unwrapped from the mandrel in a helical fashion. A problem with this method is that it only allows for the use of shape memory alloy wires or super-elastic wire without links between two adjacent rows of helical wires. Indeed, unwrapping of the wire from the mandrel is only possible when the adjacent rows are not interconnected. Additionally, a heat treatment process on the super-elastic wire is required to restore the desired shape after it has been removed from the mandrel.

A solution to these problems is presented in US patent application 2005/096729, which discloses a method for the manufacture of a stent, wherein the stent is separated from the mandrel by dissolving the mandrel. However, this method involves the use of hazardous acids, and limits the amount of materials which can be used to manufacture the stents.

Accordingly, there is a need for improved methods for the production of endoprostheses such as stents, which at least partially mitigate the problems stated above.

SUMMARY

The application provides endoprostheses, molds or mandrels for the manufacture of endoprostheses, and methods for the manufacture thereof. Methods have been developed which enable the production of molds comprising or consisting of two or more pieces, more particularly three or more pieces, which are joined via a weakened seam, such that the molds can be broken into two or more fragments in a controlled way.

The application provides methods of manufacturing a mold for an endoprosthesis, more particularly a personalized endoprosthesis fitting a patient's lumen anatomy comprising the step of meshing the mold or mandrel (or an image or model thereof), so as to determine the location of the seams forming the pieces within the mold or mold part. In particular embodiments, methods for manufacturing a mold for an endoprosthesis are provided, comprising the steps of:
  a) providing a 3D model of said mold for an endoprosthesis;
  b) meshing said 3D model, so as to divide said model into two or more solid tile pieces with seams between said tile pieces;
  c) manufacturing said mold based on the meshed 3D model, thereby providing a mold comprising solid tile pieces with seams between said tile pieces;
wherein the tile pieces are joined together at the seams with a strength which is reduced compared to the strength of said tile pieces.

In particular embodiments, the 3D model is or is based on a 3D image of said patient's lumen anatomy or part thereof. This can be of interest in the provision of a personalized endoprosthesis. Thus, in particular embodiments, the methods for manufacturing a mold for a personalized endoprosthesis fitting a patient's lumen anatomy, comprise the steps of:
  a') providing a 3D image of said patient's lumen anatomy or part thereof;
  b') optionally designing a 3D model of a mold for a personalized endoprosthesis based on said 3D image of said patient's lumen anatomy or part thereof
  c') meshing said 3D image or said 3D model, so as to divide said image or model into two or more, preferably three or more solid tile pieces and spacings or seams between said tile pieces; and
  d') optionally, manufacturing a mold based on said 3D image or said 3D model, thereby providing a mold comprising solid tile pieces interlinked through seams.

In the methods envisaged herein, the nature and/or width of the spacings or seams between the tiles is such that the tile pieces are joint together at the seams with a strength which is reduced compared to the strength of said tile pieces during manufacturing of said mold.

In particular embodiments of the methods as described herein, the mold is manufactured by additive manufacturing, more particularly by a technique such as, but not limited to stereolithography, selective laser sintering, selective laser melting and/or fused deposition modeling.

In particular embodiments, the application provides methods for generating a personalized mold for an endoprosthesis for a patient, characterized in that they comprise the steps of:
  a) providing a 3D model of a mold for an endoprosthesis based on 3D images of the patient; and b) meshing said 3D model, so as to divide said model into two or more solid tile pieces and spacings between said tile pieces;

whereby the nature and/or size of said spacings is provided such that, upon executing said model in an additive manufacturing process, the tile pieces are joint together with spacings or seams having a strength which is reduced compared to the strength of said tile pieces.

In particular embodiments of the methods of generating a mold for a personalized endoprosthesis fitting a patient's lumen anatomy as described herein further comprise the step of providing onto the surface of the mold one of or more structural features not corresponding to the patient's lumen anatomy, which features are of use in the manufacture of said endoprosthesis on said mold. More particularly such features comprise additional grooves in which one or more wires for the endoprosthesis can be positioned.

The application further provides methods for converting a 3D model into a crushable mold, which methods comprise meshing said 3D model so as to divide said model into three or more solid tile pieces with seams between said tile pieces, whereby the meshing pattern contains information such that during manufacturing of said mold, the strength of the seams is reduced compared to the strength of said tile pieces.

The application further provides methods for manufacturing a personalized endoprosthesis using the molds as provided herein. More particularly, these methods may comprise the steps of making a mold based on the patient's lumen anatomy, which mold may comprise or consist of tile pieces linked together by seams or spacings of which the strength is reduced compared to the tile pieces such that the mold can be broken in a controlled way, making the endoprosthesis on the mold and removing the mold from the endoprosthesis by breaking the mold. In particular embodiments, the methods for manufacturing a personalized endoprosthesis as described herein comprise the steps of:

a) meshing a 3D image of said patient's lumen anatomy or part thereof or a 3D model obtained therefrom, so as to divide said image or model into two or more, more particularly three or more solid tile pieces and spacings between said tile pieces;

b) manufacturing a mold based on said 3D image or said 3D model, thereby providing a mold that may comprise solid tile pieces interlinked through seams based on the model or image obtained under (a); and c) manufacturing an endoprosthesis using said mold obtained in step b) as a mandrel; and d) mechanically breaking and removing said mandrel by applying external mechanical force, thereby obtaining a personalized endoprosthesis fitting the patient's lumen anatomy.

In particular embodiments, the methods as envisaged herein thus start from a 3D image of the patient's lumen anatomy. Thus in particular embodiments, the methods comprise the steps of:

a) providing a 3D image of said patient's lumen anatomy or part thereof;

b) optionally designing a 3D model of a mold for a personalized endoprosthesis based on said 3D image of said patient's lumen anatomy or part thereof c) meshing said 3D image or said 3D model, so as to divide said image or model into two or more, more particularly three or more solid tile pieces and spacings between said tile pieces;

d) manufacturing a mold based on said 3D image or said 3D model, thereby providing a mold that may comprise solid tile pieces interlinked through seams based on the model or image obtained under (c); and e) manufacturing an endoprosthesis using said mold obtained in step d) as a mandrel; and f) mechanically breaking and removing said mandrel by applying external mechanical force, thereby obtaining a personalized endoprosthesis fitting the patient's lumen anatomy.

In particular embodiments of these methods, the mold is made by additive manufacturing.

In further particular embodiments of the methods of manufacturing a personalized endoprosthesis, the endoprosthesis is formed on the mold using laser cutting.

In particular embodiments, the step of manufacturing the prosthesis on the mold may comprise providing one or more wires for the endoprosthesis on the mold. In further particular embodiments, a first and a second wire are provided on the mold, which wires are interconnected. More particularly, the steps of providing one or more wires on the mold may comprise i) wrapping a first wire in a helical manner around the mold;

ii) wrapping a second wire in a helical manner around the mold, wherein said second wire intersects one or more times with said first wire; and iii) connecting said first and said second wire in at least some of the places where said first and second wire intersect.

In particular embodiments of the methods as described herein the material of the wires is selected from a shape memory alloy, super elastic alloy, polymer, stainless steel or any other material which is used in endovascular prosthesis.

In particular embodiments of the methods for manufacturing a personalized endoprosthesis, the step of manufacturing the endoprosthesis on the mold may comprise providing a deploy mechanism for said endoprosthesis.

Also provided herein are personalized endoprostheses obtainable by the methods described herein. More particularly, the endoprosthesis is an endovascular endoprosthesis, more particularly, a stent or a heart valve frame or a combination thereof.

Also provided herein are molds for manufacturing a personalized endoprosthesis, which molds are provided with a tiled structure, i.e. tiles interconnected at the seams, whereby the seam strength is lower than the tile strength. In particular embodiments, the molds consist of one and the same material (or combinations of material). In further particular embodiments the molds comprise at least 10 tile pieces, more particularly at least 10 tile pieces of comparable size. In further particular embodiments, the mold may consists of or may comprise a part consisting of more than 10 pieces of comparable size. The molds as envisaged herein may be used as a mandrel and can be broken into small pieces in a controlled and optionally predefined manner, which facilitates separation of the endoprosthesis and the mandrel. Furthermore, the weakened seams of the models can be made such that they do not compromise the rigidity of the mold.

BRIEF DESCRIPTION OF THE DRAWINGS

The following description of the figures of specific embodiments is merely exemplary in nature and is not intended to limit the present teachings, their application or uses. Throughout the drawings, corresponding reference numerals indicate like or corresponding parts and features.

FIG. 1—3D image of the relevant part of the patient's vessel anatomy is provided according to a particular embodiment.

FIG. 2—A model of a mold for a patient-specific prosthesis of a vessel which has been meshed according to a particular embodiment.

FIG. 3—Example of a personalized vessel endoprosthesis which can be obtained according to an embodiment.

FIG. 4—3D image of the relevant part of the patient's heart valve anatomy is provided according to a particular embodiment.

Figure 1:
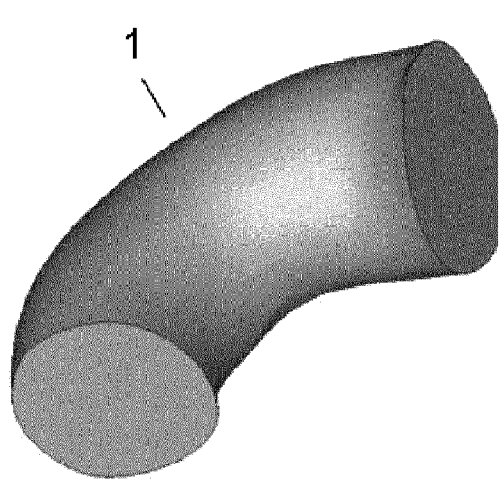

In the figures, the following numbering is used:
1—3D image of patient's lumen anatomy; 2—meshed 3D image; 3—tile pieces; 4—seams or spacings; 5—personalized vessel endoprosthesis; 6—3D image of part of a patient's heart valve anatomy; 7—meshed 3D image; 8, 9—tile piece; 10—seam

DETAILED DESCRIPTION OF CERTAIN INVENTIVE EMBODIMENTS

Reference will be made herein to particular embodiments but the concepts provided herein are not limited thereto. Any reference signs in the claims shall not be construed as limiting the scope thereof.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" when referring to recited members, elements or method steps also include embodiments which "consist of" said recited members, elements or method steps.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments described herein are capable of operation in other sequences than described or illustrated herein.

The term "about" as used herein when referring to a measurable value such as a parameter, an amount, a temporal duration, and the like, is meant to encompass variations of +/−10% or less, preferably +1-5% or less, more preferably +/−1% or less, and still more preferably +/−0.1% or less of and from the specified value, insofar such variations are appropriate to perform in the disclosure. It is to be understood that the value to which the modifier "about" refers is itself also specifically, and preferably, disclosed.

The recitation of numerical ranges by endpoints includes all numbers and fractions subsumed within the respective ranges, as well as the recited endpoints.

All documents cited in the present specification are hereby incorporated by reference in their entirety.

Unless otherwise defined, all terms used in this disclosure, including technical and scientific terms, have the meaning as commonly understood by one of ordinary skill in the art to which it belongs. By means of further guidance, definitions for the terms used in the description are included to better appreciate the teachings provided herein. The terms or definitions used herein are provided solely to aid in the understanding thereof. Reference throughout this specification to "one embodiment" or "an embodiment" means that a particular feature, structure or characteristic described in connection with the embodiment is included in at least one embodiment. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the enclosed claims, any of the claimed embodiments can be used in any combination.

Provided herein are methods for manufacturing a mold or mandrel for use in the manufacture of an endoprosthesis, particularly an intraluminal endoprosthesis.

The molds obtainable by these methods are particularly suitable for the manufacture of custom or personalized endoprostheses, more specifically an endoprosthesis which is adapted to a patient's anatomy. Thus, provided herein are methods for manufacturing a mold for the manufacture of an endoprosthesis specifically fitting a patient's lumen anatomy. Custom endoprostheses reduce the risk of suboptimal intervention results compared to standard endoprostheses, especially when the lumen anatomy has a high rate of curvature and/or a non-uniform diameter, as is the case with coronary arteries, cerebral vessels, intestines, etc. For example, custom intraluminal prostheses may have a shape and size which are complementary to the shape and size of the patient's lumen of interest. The patient may be a human or animal patient.

The terms "mold" and "mandrel" are used interchangeably herein and refer to three dimensional objects of which the shape and surface is made specifically such that it can be used to ensure a desired shape and surface in an object manufactured thereon. The term "endoprosthesis" refers to any prosthetic device placed within the body. The term "intraluminal prosthesis" refers to any prosthetic device placed within a lumen, vessel or duct of the body. The term "lumen" refers to any cavity or passageway within the body, and particularly refers to the inside space of a tubular structure, for example the inside space of an artery, intestine, etc.

An intraluminal endoprosthesis is typically an expandable prosthesis for implantation into a body lumen and includes devices such as stents, grafts, stent-grafts, vena cava filters, tubular expandable frameworks, heart valve frames, a heart valve with a stent etc. The therapeutic objective may include but is not limited to the objective of restoring or enhancing flow of fluids through a body lumen or duct. The objective may alternatively be the prevention of flow of fluid or other material through the body lumen.

Accordingly, also provided herein are molds which are manufactured based on a 3D image of the anatomy of the patient's lumen. The mold for the endoprosthesis will correspond to a 3D model of the patient's lumen such that the endoprosthesis can be made thereon. Thus, optionally, the methods as described herein may include a step of obtaining a 3D image or representation of a patient's lumen anatomy; this is the lumen wherein the endoprosthesis will be positioned. A 3D model can be obtained directly from this 3D image, for example obtained via the Mimics™ or 3-matic™ computer program as provided by Materialise N.V., Leuven, Belgium. Thus in particular embodiments of the methods provided herein, a 3D model is made for the mold based on the 3D image. In particular embodiments of the methods as provided herein, small modifications can be made to the 3D image to make the model for the mold. For example, certain narrowings of the lumen may be widened compared to the original 3D image, such that the adapted 3D image corresponds to a desired optimal lumen anatomy. In particular embodiments, the size of the lumen image is enlarged or reduced locally, in function of the local pressure which needs to be provided by the endoprosthesis.

Thus the methods may comprise the step of designing a 3D model of a mold for a personalized endoprosthesis based on a 3D image of the patient's lumen anatomy or part thereof. In alternative embodiments, the 3D image can be used directly as the 3D model.

The 3D model of the mold is then divided into two or more, more particularly three or more sub-domains, which are herein referred to as "tile pieces" or "tiles". This process is referred to as meshing. The object of the meshing process is to determine how the mold can be broken, i.e. which pieces will be formed, and optionally in what order. More particularly, the object can be to ensure that the mold is broken into two or more, more particularly three or more fragments in a controlled way, such that the mold can be removed from the endoprosthesis (see further). Therefore, the 3D image or model is meshed at least in those areas where the corresponding mold will need to be broken e.g. where it is expected to be difficult to remove from the endoprosthesis. In certain embodiments, the tile pieces are similar pieces, preferably pieces with a similar size, even more preferably pieces with a similar size and shape. However, as will be detailed below, the pieces may differ in size and shape.

In the methods envisaged herein, the meshed mold or image is used as a basis during the manufacturing process to ensure the production of the mold in "pieces" which are separated (while remaining connected to each other) by "spacings". These spacings are in fact not openings (though it is not excluded that they may contain one or more openings, provided that it is not over the entire length thereof) but (typically linear) areas of the mold having different properties than the tiles which they interconnect. Indeed, as will be detailed below, the mold is manufactured such that at the joints of the tile pieces, i.e. the spacings, the strength of the mold is reduced compared to the tile pieces themselves. This ensures that, when pressure is put on the mold or particular parts thereof, it can be broken in a controlled way. The spacings which extend in one and the same line form "seams" in the mold. In particular embodiments, the meshing involves the provision of at least two independent seams. In particular embodiments, the meshing involves the provision of at least two seams which are not parallel. Most particularly, the meshing involves the provision of at least two seams which intersect.

Provided herein are methods for manufacturing a mold or mold part whereby the mold is provided as a three or more, more particularly a plurality of pieces or tiles, which are connected through seams, which seams can be broken when the mold is subjected to a manual pressure. More particularly, the methods as described herein comprise the step of meshing the mold or mold part (or an image or model thereof), so as to determine the location of the seams forming the pieces making up the mold or mold part.

In particular embodiments, the meshing is performed without changing the outline of the model. For example, when providing parallel seams, the meshing can be compared to "removing" one or more thin slices from the image, such that the remaining tile pieces are separated by spacings at the original location of the removed slices.

Accordingly, in particular embodiments, the methods as provided herein involve meshing the image or the model of the mold so as to divide it into two or more, more particularly three or more tile pieces and spacings between said tile pieces, preferably without changing the relative position of the tile pieces and/or the outline of the image.

The shape and size of the tiles is not critical to the meshing step or the finalized meshed mold. As indicated above, in particular embodiments, the individual tiles have the same shape and size. However, the individual tile pieces may vary in shape or form according to the required specifications of the mold and/or endoprosthesis and/or its envisaged breaking. The tile pieces may form a structured or unstructured mesh. A structured mesh is characterized by regular connectivity that can be expressed as a two or three dimensional array. An unstructured mesh is characterized by irregular connectivity. In preferred embodiments, the tile pieces form a structured mesh.

In certain embodiments, the tile pieces are essentially geometric pieces such as triangles, squares, rectangles, pentagons and/or hexagons. Thereby, the tile pieces ensure a tiled structure of the mold. Also combinations of these shapes and/or other suitable geometries may be considered. In further embodiments, the tile pieces are triangular, square, rectangular, pentagonal and/or hexagonal prisms. Typically, the overall shape and size of the tile is determined by the desired requirements and impact of breaking the mold (i.e. the amount of pressure to be applied and the resulting pieces to be generated).

It is envisaged that in particular embodiments the tile pieces at one or more surfaces of the mold have a different shape than the tile pieces which are more removed from the border of the mold. Therefore, in particular embodiments, at least 20, 30, 40, 50, 60, 70, 80 or 90 percent of the tile pieces have a similar or identical shape.

Additionally or alternatively, it is envisaged that the shape of the tiles making up the outer surface of the mold for the endoprosthesis is not geometrical. Indeed, typically the interconnecting sides of the tiles will be have a geometrical or regular shape, while the shape of the tile which is intended to contact the endoprosthesis is not.

The number of tile pieces provided in the image or model of the mold during the meshing process and thus in the manufactured mold, depends on various factors such as the size and shape of the mold and/or the endoprosthesis to be made and/or the envisaged breaking conditions. More particularly, it can depend on the size of the mold. For example, where the mold is for a hollow tubular endoprosthesis such as a stent, the size of the tile can be chosen such that it allows easy removal of the tile pieces through an opening of the tube. In certain embodiments, the model is provided with three, five, ten, twenty, fifty, hundred or more tile pieces. In particular embodiments, the meshing ensures the provision of at least 5 tile pieces in the mold, more particularly at least ten tile pieces in the mold, more particularly at least 20 pieces.

The meshing into at least three tile pieces implies the presence in the mold (or mold part) of at least two independent seams interlinking the different tile pieces, such that, if desired, pressure can be applied selectively to only one and not another seam. In particular embodiments, the independent seams are in different orientations. Thus, the mold does not need to be broken along a predefined seam (e.g. which is the case when a single weakened seam would be provided), but the can be broken by the user along a seam as chosen by the user. This allows a user defined breaking of the mold. Similarly, the size of the tile pieces provided in the mesh will be determined by the nature of the object and the envisaged breaking pattern thereof. In certain embodiments, the tile pieces have a size between 2 mm2 and 10 mm2. In particular embodiments, the mold surface may comprise between 0.25 and 25 tile pieces per cm2. However by using state of the art technologies such as laser micro sintering, the resolution of the manufactured molds can be reduced below the limits commercial SLS devices, providing resolution of less than 30μηι. Accordingly, in certain embodiments, the tile pieces may have a typical surface dimension below 2 mm2 and typically ranging from 250 μηι2 to 4 cm2.

In some embodiments it is envisaged that all or most of the pieces have a similar size, more particularly sizes which differ at most by 5-10%. In particular embodiments, the meshing step ensures the provision of at least three, more particularly at least 4, most particularly 5 or more pieces and typically more than 10 pieces whereby all or most of the pieces have a similar size, more particularly sizes which differ at most by 5-10%. Typically, while in certain embodiments, only part of the mold may be meshed, the meshed area will comprise of at least three pieces whereby all of the pieces have a similar size.

In particular embodiments, the tiles discussed above can be connected (or separated) by spacings or seams. The spacings or seams between adjacent tile pieces can have planar geometry and can have a uniform width. Consequently, in particular embodiments, the neighboring surfaces of two adjacent pieces or tiles can have a planar geometry.

However, the spacings or seams and neighboring surfaces may also have other shapes and/or may have a non-uniform width. In particular embodiments, the adjoining surfaces of the tiles have a curved, jagged, serrated, corrugated or notched shape or geometry. In particular embodiments, the seams or spacings have a uniform width. An important advantage of non-planar adjoining surfaces of the tiles is their enlarged area compared to when the adjoining surfaces are planar. This allows engineering of the seams to a certain intended breaking force. Indeed, the seam surface strongly influences the seam strength. Additionally or alternatively, these shapes may provide seams with different strength in different directions. Furthermore, gaps with a non-uniform width may provide tailored strong and weak areas within the seams.

Thus, by determining the number, shape and size of the tiles in the mold and the width of the seams between them, the breaking of the mold upon applying pressure is controlled.

Typically the desired strength of the seams is such that it is breakable by hand and typically ranges between 1 to 100 N and preferably between 1 and 50 N.

The application further provides method for generating a breaking pattern on an endoprosthesis mold for additive manufacturing, the method may comprise meshing a 3D model of the endoprosthesis or a part thereof, so as to divide said model or part thereof into three or more tile pieces interlinked through seams, whereby the width of the seams and/or their method of manufacture is such that their strength is reduced compared to the strength of the tile pieces. The application thus also provides methods for converting a 3D model into a crushable mold, which method may comprise meshing said 3D model so as to divide said model or part thereof into three or more solid tile pieces with seams between said tile pieces, whereby the meshing pattern contains information such that during manufacturing of said mold, the strength of the seams is reduced compared to the strength of said tile pieces.

The design of the meshing in the methods envisaged herein is specifically adapted to the method of manufacturing the object. Most particularly, the method of manufacturing is by additive manufacturing. (AM, see further). More particularly, the object is manufactured by generating the tile pieces interconnected by seams during manufacturing. Typically, an AM apparatus builds objects on a layer-by-layer basis. The provision of the seams between the tile pieces can be ensured in different ways, and can be dependent on the AM method used. In particular embodiments, the seams are ensured by sintering only the tile pieces, while not sintering at the location of the envisaged seams. Provided the width of the seams is chosen correctly, the individual tile pieces will nevertheless be interlinked, but the strength of the object at the seams between the tile pieces is reduced compared to the strength of the tile pieces. The reason for this is that the thermal energy provided by a laser onto the powder material will also cause some sintering of the powder surrounding the individual tile pieces. The result is that neighboring tile pieces manufactured sufficiently close to each other will stick together. In alternative embodiments, the laser is also applied to the particles or powder at the locations corresponding to the spacings or seams between the tile pieces, whereby the (laser) power delivered to the particles or powder at the locations corresponding to the spacings is lower than the power delivered to the particles or powder at the locations corresponding to the tile pieces. This still results in areas with different degrees of sintering of the powder (i.e. the tile pieces and the seams) and thus different strength, but provides a better control of the seam strength.

In particular embodiments, the design of the meshing may also involve determining the optimal orientation of the meshing. Indeed, typically during AM manufacturing the AM apparatus proceeds in a direction perpendicular to the individual layers. It has been found that, in particular embodiments, the reproducibility of the seam properties increases when the seam direction is parallel to the direction in which the AM apparatus proceeds; this is the direction perpendicular to the layers of which the object is built. Therefore, in particular embodiments, the spacings or seams between the tile pieces are designed such that they are parallel to the direction in which the AM apparatus proceeds. In particular embodiments, this implies that the orientation of the object when manufactured is adjusted to ensure that the seams are generated in a direction which is parallel to the direction in which the AM apparatus proceeds. It has further been observed that an alteration of the build direction can be used to change the strength of the bond between the tiles. As a result of this and in order to maintain the same structural strength throughout the object, the spacing can also be adjusted between different orientations. For example an object can be provided having 0.1 mm thick seams for perpendicular tiles and 0.2 mm thick seams for parallel tiles.

Thus in particular embodiments, the design of the meshing involves selecting the width size of the seams based on the orientation of the seam within the object.

As a result, in particular embodiments, the width of the spacings between the tile pieces in the meshed model depends on the orientation of the spacings. This allows to increase or decrease the strength of the object in particular directions. Additionally or alternatively, this may be used to compensate for the effects of the directionality of the additive manufacturing process as described herein above.

In particular embodiments, the strength of the seams is adjusted based on a desired breaking pattern of the mold. Thus, it can be envisaged to ensure breaking of some parts before others, e.g. to avoid clogging of mold with mold pieces.

The application thus further provides computer programs which have the potential, to bring about, when run on a computer, the methods for meshing a 3D model of an object and computer-readable media which comprise information relating to the implementation of a meshed 3D model in an additive manufacturing process.

The methods for providing a mold of an endoprosthesis as envisaged herein may further also comprise a step involving the actual manufacturing of the mold based on the 3D image or model obtained as described above. This is done such that a 3D mold is obtained comprising solid tile pieces interlinked through seams.

In particular embodiments the tile pieces are manufactured by additive manufacturing. Additive Manufacturing can be defined as a group of techniques used to fabricate a tangible mold of an object typically using three-dimensional (3-D) computer aided design (CAD) data of the object. Currently, a multitude of Additive Manufacturing techniques is available, including Selective Laser Sintering, stereolithography, Fused Deposition Modeling, foil-based techniques, etc.

Selective laser sintering (SLS) and selective laser melting use a high power laser or another focused heat source to sinter or weld small particles of plastic, metal, or ceramic powders into a mass representing the 3-dimensional object to be formed. Fused deposition modeling and related techniques make use of a temporary transition from a solid material to a liquid state, usually due to heating. The material is driven through an extrusion nozzle in a controlled way and deposited in the required place as described among others in U.S. Pat. No. 5,141,680. Foil-based techniques fix coats to one another by means of gluing or photo polymerization or other techniques and cut the object from these coats or polymerize the object. Such a technique is described in U.S. Pat. No. 5,192,539.

Typically AM techniques start from a digital representation of the 3-D object to be formed. Generally, the digital representation is sliced into a series of cross-sectional layers which can be overlaid to form the object as a whole. The AM apparatus uses this data for building the object on a layer-by-layer basis. The cross-sectional data representing the layer data of the 3-D object may be generated using a computer system and computer aided design and manufacturing (CAD/CAM) software.

Typically, an AM apparatus builds objects on a layer-by-layer basis. Thus, the AM apparatus proceeds in a direction perpendicular to the individual layers. It is described herein that, in particular embodiments, the reproducibility of the seam properties increases when the seam direction is parallel to the direction in which the AM apparatus proceeds; this is the direction perpendicular to the layers of which the object is built. Therefore, in particular embodiments, the spacings or seams between the tile pieces are designed such that they are parallel to the direction in which the AM apparatus proceeds. In particular embodiments, this implies that the orientation of the mold when manufactured is adjusted to ensure that the seams are generated in a direction which is parallel to the direction in which the AM apparatus proceeds. The inventors have further found that an alteration of the build direction can be used to change the strength of the bond between the tiles. As a result of this and in order to maintain the same structural strength throughout the mold, the spacing can also be adjusted between different orientations. For example a mold can be provided having 0.1 mm thick seams for perpendicular tiles and 0.2 mm thick seams for parallel tiles.

In particular embodiments, the width of the spacings between the tile pieces depends on the orientation of the spacings. This allows to increase or decrease the strength of the mold in particular directions. Additionally or alternatively, this may be used to compensate for the effects of the directionality of the additive manufacturing process as described herein above.

Thus in particular embodiments, methods are provided which comprise manufacturing the mold by additive manufacturing, thereby providing a mold that may comprise two or more, more particularly three or more, tile pieces and spacings or seams between said tile pieces which have a reduced strength compared to the tiles. In particular embodiments, the tile pieces are manufactured according to the meshed model, i.e. such that they are set in a position relative to each other corresponding to their position in the model, and preferably without changing the outline of the mold. The meshing effect in the manufacturing process is ensured by varying certain parameters of the process used at the position of the seams compared to the parameters at the position of the tiles.

In particular embodiments, the mold is manufactured by SLS. Using SLS, the mold can be manufactured by sintering only the tile pieces. Provided the seam is kept sufficiently narrow, the tiles remain interlinked at the seams but the strength of the mold at the seams is reduced compared to the strength of the tile pieces. The thermal energy provided by a laser onto the powder material will also cause some sintering of the powder surrounding the individual tile pieces so that they remain connected. As however, less material is sintered, the strength of the seams will be weaker than the strength of the tile pieces. Thus, even though the laser of the SLS device is not specifically applied to the particles or powder at the locations corresponding to the spacings or seams in the mold, the particles or powder at these locations still are sintered, albeit less than the sintered particles or powder forming the tile pieces of the mold.

In alternative embodiments, the laser is also applied to the particles or powder at the locations corresponding to the spacings between the tile pieces, but the (laser) power delivered to the particles or powder at the locations corresponding to the spacings or seams is lower than the power delivered to the particles or powder at the locations corresponding to the tile pieces. This also still results in areas with different degrees of sintering of the powder (i.e. the tile pieces and the seams) and thus different strength, but provides a better control of the seam strength.

The molds as can be obtained by the methods described herein comprise two or more, particularly three or more tile pieces which are linked by weakened seams. The weakened seams allow breaking of the mold in a controlled and predefined way, which facilitates removal of the endoprosthesis from the mold (see further). Another advantage is that the weakened seams can be made such that they do not compromise the rigidity of the mold. Therefore, the seams do not increase the risk of mold deformation during the manufacture of the endoprosthesis.

In particular embodiments, the width of the spacings or seams between the tile pieces is chosen such that the tile pieces are linked by the seams during manufacturing of the tile pieces, wherein the seam strength is reduced compared to the strength of the tile pieces. Indeed, together with the seam surface area, the width of the seams or spacings or seams between the tile pieces is an important parameter which influences the seam strength. If the spacings or seams are too narrow, the seams will be too strong, which makes it difficult to break the mold in a controlled manner. On the other hand, if the spacings or seams are too wide, the seams between the tile pieces will be too weak, or the tile pieces won't be joined together at all.

The optimal dimensions of the spacings or seams between the individual tile pieces in the mold depend on various parameters such as the required seam strength, the material of which the mold is made, the (additive) manufacturing technique and the resolution of the additive manufacturing device (3D printer). In particular embodiments, the thickness of the seams between the tile pieces ranges between 0.01 and 1 mm, preferably between 0.02 and 0.5 mm, and more preferably between 0.05 mm and 0.5 mm. Accordingly, in particular embodiments, the image is meshed in step b) such that the spacings or seams between the individual tile pieces have a width between 0.01 and 1 mm. However by using state of the art technologies such as laser micro sintering, the resolution of the manufactured molds can be reduced below the limits commercial SLS devices, providing resolution of less than 30μηι. Accordingly, in certain embodiments, the thickness of the seams between the tile pieces ranges between 1μηι and 1 mm. Particular embodiments of the breakable molds are provided in patent application EP 11184363.7 (which is incorporated herein by reference).

Additive manufacturing is particularly useful for the manufacture of hollow objects. Accordingly, in certain embodiments, the mold for an endoprosthesis is hollow. This reduces the amount of material necessary to make the mold. A hollow mold is also easier to break, which facilitates removal of the endoprosthesis from the mold (see further).

The molds envisioned herein and obtainable as described above can be used as a mandrel in the manufacture of a custom endoprosthesis. Accordingly, methods are also provided herein for manufacturing an endoprosthesis fitting the patient's lumen anatomy, making use of the molds as described herein. More particularly these methods comprise the manufacture of a mold as described herein and further the manufacture of an endoprosthesis on said mold. In particular embodiments, the methods for the manufacture of an endoprosthesis comprise the steps of:

a) optionally, providing a 3D image of said patient's lumen anatomy;

b) meshing said 3D image, or a model obtained therefrom, so as to divide said image into two or more tile pieces and spacings or seams between said tile pieces;

c) manufacturing a mold based on said meshed 3D image or model, thereby providing a mold that may comprise solid tile pieces interlinked through seams; and d) manufacturing an endoprosthesis using said mold obtained in step c) as a mandrel; and e) mechanically breaking and removing said mandrel by applying external mechanical force, thereby providing a personalized endoprosthesis fitting the patient's lumen anatomy.

In particular embodiments, the 3D image is first used to generate a 3D model of the mold. Accordingly, in particular embodiments, the methods for the manufacture of an endoprosthesis that may comprise:

a) providing a 3D image of said patient's lumen anatomy or part thereof;

b) optionally designing a 3D model of a mold for a personalized endoprosthesis based on said 3D image of said patient's lumen anatomy or part thereof c) meshing said 3D image or said 3D model, so as to divide said image or model into two or more solid tile pieces and spacings or seams between said tile pieces;

d) manufacturing a mold based on said 3D image or said 3D model, thereby providing a mold that may comprise solid tile pieces interlinked through seams;

e) manufacturing an endoprosthesis using said mold obtained in step d) as a mandrel; and f) mechanically breaking and removing said mandrel by applying external mechanical force, thereby providing a personalized endoprosthesis fitting the patient's lumen anatomy.

Thus methods for manufacturing an endoprosthesis are similarly based on 3D images of the patient's anatomy and contain steps which are comparable to the steps for manufacturing a mold as described herein above. In steps d) and e), the mold obtained in step c) is used for the manufacture of a personalized endoprosthesis.

In the methods for manufacturing an endoprosthesis as described herein, the mold is used as a mandrel. Mandrels may be used in the manufacture of endoprostheses such as stents in different ways. For example, stents may be manufactured by twisting a wire in a helical pattern around a mandrel. Patents U.S. Pat. No. 7,722,663 and EP 0556850 show how stents can be manufactured by twisting an undulating wire in a helical pattern around a mandrel. Alternatively, stents may also be manufactured by laser cutting a tube. An example of a method of manufacturing a metal stent with a laser is the method explained in U.S. Pat. No. 5,780,807. Herein, a mandrel is placed inside the lumen of metal tubing, whereby the mandrel provides structural support to the tubing as it is may be cut and shaped.

Accordingly, in particular embodiments, the step of manufacturing an endoprosthesis on the mold or mandrel that may comprise providing one or more wires for the endoprosthesis. In further embodiments, the methods may comprise twisting one or more wires in a helical pattern around the mandrel. In particular, the step of manufacturing an endoprosthesis on the mold or mandrel that may comprise providing a single wire for the endoprosthesis.

More particularly, the methods for manufacturing an endoprosthesis using the mold as a mandrel may comprise the steps of:

i) wrapping a first wire in a helical manner around the mandrel;

ii) wrapping a second wire in a helical manner around the mandrel, wherein said second wire intersects one or more times with said first wire; and iii) connecting the first and second wire in at least some of the points of intersection between the two wires; i.e. one or more points at which a portion of two or more wires cross, overlap or come near to or in actual contact with one another.

In particular embodiments, the first and second wire are connected in all of the points of intersection between the two wires. Suitable means of connecting may include by welding, tying, knitting, thermal melt, chemical bond, adhesive, sintering, or any means known in the art.

The methods of manufacturing an endoprosthesis thus may involve applying a wire on the mandrel. The manner in which the wire is twisted around the mandrel may be of importance for certain endoprosthesis properties, such as its flexibility and ability to self-expand. Therefore, in these embodiments, it is important that the wires are positioned on the mandrel in a correct way. In particular embodiments, the methods for manufacturing an endoprosthesis as envisaged herein further comprise the step of providing onto the mold a reference structure. In particular embodiments, the reference structure indicates the optimal position of the endoprosthesis on the mold. In certain embodiments, the reference structure may comprise grooves in which in which one or more wires for manufacturing the endoprosthesis can be positioned. In particular embodiments, the meshing of the image or model of the mold is ensured such that the spacings or seams between the tile pieces correspond at least partially to these grooves.

In certain embodiments, the mold is provided with a reference structure after it has been manufactured. For example, the mold may be provided with grooves using laser cutting, milling or any other useful methods. In other embodiments, the reference structure is provided on the (meshed) image and this structure is taken into account upon manufacturing the mold. As a result, the generated mold may comprise the reference structure, thus avoiding the extra step of laser cutting, milling, etc. as described herein above. This method is of particular interest when the mold is made by additive manufacturing.

In particular embodiments, an endoprosthesis may be manufactured by applying (computer controlled) laser cutting or another high precision technique to a tube. Accordingly, methods for providing an endoprosthesis on a mandrel as envisaged herein may also comprise manufacturing an endoprosthesis using laser cutting. In order to obtain a custom endoprosthesis, the tube is provided on the mandrel. For example, this may be obtained by coating the mandrel with a suitable material. Alternatively, a tube with a larger diameter than the mandrel can be slid onto the mandrel, followed by crimping of the tube, as described in U.S. Pat. No. 7,530,253 which is hereby incorporated by reference. Particularly, the endoprosthesis may be manufactured by using shape memory alloys or any other material type, including stainless steel.

The endoprosthesis obtained on the mandrel in each one of the methods described herein will need to be removed from the mandrel before it can be used. However, as custom (intraluminal) endoprostheses typically have complex shape and/or non-uniform size, it is not always possible to remove the mold from the endoprosthesis without damaging or changing the shape of the endoprosthesis. For example, the mandrel may be curved and/or have a varying diameter. In the prior art it has been suggested to remove the wires from the mandrel before connecting the wires at the intersections. However, this requires an additional heat treatment of the wires after removal from the mandrel. Moreover, the connection of the wires is generally easier when the wires are supported by the mandrel.

In the methods envisaged herein, the endoprosthesis can be removed from the mandrel by mechanically breaking the mandrel by applying (external) mechanical force. Indeed, as the mold is made of tile pieces interlinked by weakened seams, the mandrel can be broken in a controlled way. In particular embodiments this implies that they can be broken in a user-defined way and/or that the individual tile pieces can be removed easily from the endoprosthesis. The control can relate to the size of the parts that are generated (i.e. tiles) and/or to the way the mandrel is broken (i.e. gradually or all at once).

Because the mandrel can be removed without affecting the endoprosthesis manufactured thereon, the wires can be connected before they are removed from the mandrel. Moreover, endoprosthesis removal does not involve the use of hazardous acids.

The material used to manufacture the mandrel may depend on the (additive) manufacturing method used and the specifications of the endoprosthesis to be manufactured. In particular embodiments, the mandrel is made of a material which is compatible with additive manufacturing, including polymeric materials, metals, metal alloys, ceramic materials and glass. In preferred embodiments, the mold is made of polyamide, polystyrene, steel, titanium, or aluminum. The mold may also be made of a composite material, preferably glass-filled polyamide or alumide. Alumide is a blend of polyamide and aluminum powder. Typical mold (part) materials include for instance DSM Somos® series of materials 7100, 8100, 9100, 9420, 10100, 1 1100, 121 10, 14120 and 15100 (from DSM Somos); ABSplus-P430, ABSi, ABS-ESD7, ABS-M30, ABS-M30i, PC-ABS, PC-ISO, PC, ULTEM 9085, PPSF and PPSU materials (from Stratasys); Accura Plastic, DuraForm, CastForm, Laserform and VisiJet line materials (from 3-Systems); Aluminium, CobaltChrome and Stainless Steel materials, MarangingS teel, Nickel Alloy, Titanium, the PA line of materials, PrimeCast and PrimePart materials and Alumide and CarbonMide (from EOS GmbH).

The material used to manufacture the endoprosthesis is preferably chosen from but not limited to shape memory alloy, super elastic alloy, polymer, stainless steel or any other material which is used in endovascular prostheses. In particular embodiments, the material is a shape memory and/or super elastic material, including metals, metal alloys and polymers. In particular embodiments, the wires used for making the endoprosthesis comprise nitinol, stainless steel, titanium, platinum, pyrolitic carbon, polyglycolic acid, expanded polytetrafluoroethylene, polyethylene terephtalate, polylactic acid or any other (biocompatible) metal, ceramic or polymer known in the art.

The (intraluminal) endoprosthesis envisaged herein may be self-expanding or balloon expandable. A self-expanding endoprosthesis has the ability to revert readily from a reduced profile configuration to a larger profile configuration in the absence of a restraint upon the device that maintains the device in the reduced profile configuration. Balloon expandable refers to a device that may comprise a reduced profile configuration and an expanded profile configuration, and undergoes a transition from the reduced configuration to the expanded configuration via the outward radial force of a balloon expanded by any suitable inflation medium.

In particular embodiments, the endoprosthesis is a self-expanding prosthesis. Accordingly, in certain embodiments, the methods for manufacturing an endoprosthesis may further comprise the step of providing a deploy mechanism for the endoprosthesis.

For example, the endoprosthesis may be provided with hook-like elements or other elements which facilitate deployment. Accordingly, in certain embodiments, the mold may comprise recesses for accommodating deployment elements of the endoprosthesis and the methods for providing the molds as described herein comprise the step of introducing into the 3D model, features for accommodating deployment elements during the manufacture of the endoprosthesis thereon.

In particular embodiments, the methods for manufacturing an endoprosthesis may comprise the step of coating the endoprosthesis. Different types of suitable coatings are known in the art. In particular embodiments, the coating is an (inert) coating selected from the group consisting of polysulfone, silicone rubber, polyurethane, synthetic glycocalix, amorphous silicon carbide, diamond-like carbon, magnesium phosphate, magnesium oxide, or mixtures thereof.

The application also provides molds for use in the manufacturing of an endoprosthesis, more particularly a personalized endoprosthesis. The molds as envisaged herein comprise a tiled structure whereby the tiles and the seams between the tiles are made of the same material, and the seam strength is lower than the tile strength. Thus, the molds as envisaged herein typically have a surface which has a meshed appearance. However, typically both the tiles and the seams interconnecting the tiles are solid, i.e. they form a continuous surface of the mold. It may however in some embodiments be envisaged that some or all of the tiles contain an opening. In these embodiments, however, the opening will either not encompass the entire surface of the tile or may not be present on all of the tiles, so as not to compromise the rigidity of the mold.

In particular embodiments, the application provides molds or parts thereof, such as those obtainable by the methods as described herein that may comprise at least 3, 4, 5, 6, 8, 10 or more tiles interlinked through seams, whereby the nature or size of the seams is such that their strength is reduced compared to the strength of the tile pieces. In particular embodiments, the tiles of the mold have essentially the same size. More particularly, the mold or part thereof may comprise at least 10 tiles having essentially the same size. Thus, the molds envisaged herein may comprise three, or more, more particularly four or more up to a multitude of tile pieces which are linked by at least two independent weakened seams. The presence of more than one weakened seam may allow selective breaking of the mold.

In certain cases, the difficulties in mold removal may arise only in some areas and not in others. In those cases, it may be advantageous to provide a mold having different parts (i.e. connected by independent seams), wherein at least one part is meshed and the other is not, whereby the meshed part corresponds to the area(s) of the mold where difficulties for removal are expected. An advantage of such a mold may be that only a small part of the mold has to be broken whereas the rest of the mold can be maintained (and optionally reused). In particular embodiments, the different mold parts are connectable to each other, for example via coupling features providing a snap-fit system, a pinned system, a dovetail system or the like.

As detailed for the methods above, the size and shape of the tiles provided in the molds envisaged herein will be determined by the application of the mold and the envisaged breaking thereof. It will be understood that the options described above for the envisaged methods of manufacture correspond to the options envisaged for the molds.

In particular embodiments, the mold is a mold for an endoprosthesis, more particularly an endovascular endoprosthesis, such as but not limited to, a stent or a heart valve frame or a combination thereof. In view of their application as mold or mandrel, the shape of the molds envisaged herein typically correspond to at least part of the shape of the lumen.

Indeed in particular embodiments, the molds as envisaged herein are for use in the manufacture of a personalized endoprosthesis, i.e. a prosthesis of which the shape and/or surface is specifically adapted to fit the patient's lumen anatomy. This can be achieved by making the mold based on a 3D image of the patient's lumen anatomy. By manufacturing the endoprosthesis so as to tightly fit on the personalized mold, the resulting endoprosthesis will also have a personalized structure and fit. Thus, in particular embodiments, the molds envisaged herein have a shape or at least part thereof which corresponds to or matches the patient's lumen anatomy.

Typically, the provision of a mold based on a 3D image of the patient's lumen anatomy involves the use of additive manufacturing techniques. Thus, in particular embodiments, the molds envisaged herein are made by additive manufacturing. This also allows the provision of the mold and its meshed structure as a one-piece object. More particularly the molds are made by layer manufacturing processes that selectively melt material with a laser or a similar "point" source, such as the SLS, SLM or the DMLS processes and more preferably SLS. Preferred materials for such layer manufacturing processes such as SLS include Nylon-12 and composites of Nylon-12 and various additives. In particular embodiments the molds are made by SLS and consist of a sintered powder. Accordingly, in specific embodiments, the tiles and the seams between the tiles consist of a sintered (and/or cross-linked) powder, whereby the degree of sintering (and/or cross-linking) in the tiles is higher than in the seams.

Also provided herein is an endoprosthesis, more particularly a personalized endoprosthesis, obtained or obtainable by the method as described herein above.

In certain embodiments, the endoprosthesis is an intraluminal, more particularly an endovascular prosthesis. In further embodiments the prosthesis is a stent or stent graft. In certain embodiments, the endoprosthesis is a heart valve frame, or a valve with a stent.

The length and diameter of the endoprosthesis as described herein depends on the anatomy of the lumen into which it is to be deployed. For example, coronary stents typically have a length between 10 and 30 mm and a diameter (when deployed) between 2 and 5 mm, whereas a thoracic endoprosthesis typically has a length between 10 and 20 cm and a diameter between 25 and 40 mm.

In particular embodiments the endoprosthesis is partially covered by a graft material such as but not limited to an engineered, animal, human or tissue. In further particular embodiments, the endoprosthesis is a heart valve and may comprise an engineered heart valve (i.e. of human or animal material) integrated into the structure.

The concepts disclosed herein are illustrated by the following non-limiting embodiments.

EXAMPLES

Embodiment 1—manufacturing of a patient-specific stent for a blood vessel

In this embodiment, a mold for a patient-specific endoprosthesis for a blood vessel is provided.

Figure 2:
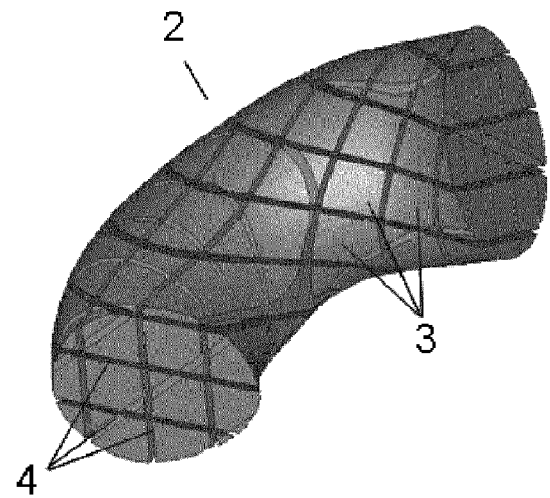

In a first step, a 3D image of the relevant part of the patient's vessel anatomy is provided (FIG. 1). This is used as a model for the mold. In a next step the 3D model is meshed, dividing the model into multiple tile pieces which are separated by spacings (FIG. 2). The meshing basically corresponds to slicing the model up in at least two orientations. The resulting tiles are essentially geometrical in shape, and most tiles are of a similar size. The seams or spacings in this embodiment are of essentially the same width. The width is selected such that when manufacturing the mold using SLS, sintering only the tile pieces will nevertheless cause the powder material at the seams to be sintered such that the tiles are connected. However, as the thermal energy provided on the powder at the seams is more limited than at the tiles, the strength of the mold at the seams is reduced compared to the strength of the tile pieces.

In a next step the mold is manufactured based on the meshed model, i.e. allowing the laser to sinter the powder only directly in the areas of the tiles, such that a mold is generated that may comprise tile pieces interlinked through seams as provided in the meshed mold model.

Figure 3:
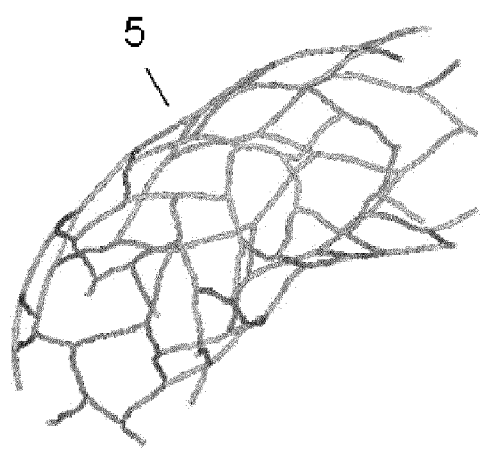

In yet a next step the endoprosthesis mold is used as a mandrel to produce a personalized stent for the patient. After the endoprosthesis is made, the mold is removed by applying a force on the mold, such that the mold breaks at the seams and falls apart in tiles. The finished prosthesis is obtained therefrom (FIG. 3).

Embodiment 2—manufacturing of a mold for a patient-specific endoprosthesis for a blood valve.

In this embodiment, a mold for a patient-specific endoprosthesis for a blood valve is provided.

Figure 4:
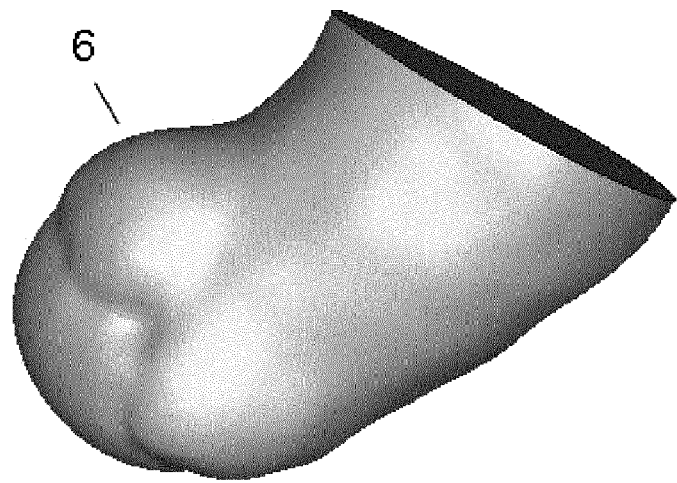
Figure 5:
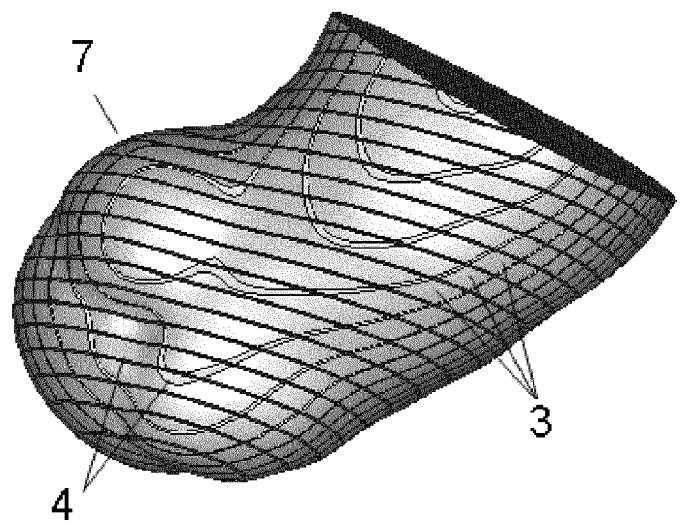
FIG. 5—A model of a patient-specific mold of a heart valve which has been meshed according to a particular embodiment.

Similar to the embodiment described above, a 3D image of the relevant part of the patient's valve anatomy is provided (FIG. 4). This is used as a model for the valve mold. In a next step the 3D model is meshed, dividing the model into multiple tile pieces which are separated by seams or spacings (FIG. 5). The resulting tiles are essentially geometrical in shape, and most tiles are of a similar size. The width and/or shape of the seams is selected such that upon manufacturing the mold, the strength of the mold at the seams is reduced compared to the strength of the tile pieces.

In a next step the mold is manufactured based on the meshed model of the valve such that a valve mold is generated that may comprise tile pieces interlinked through seams as provided in the meshed valve mold model.

Example of seams with non-uniform thickness.

Figure 6:
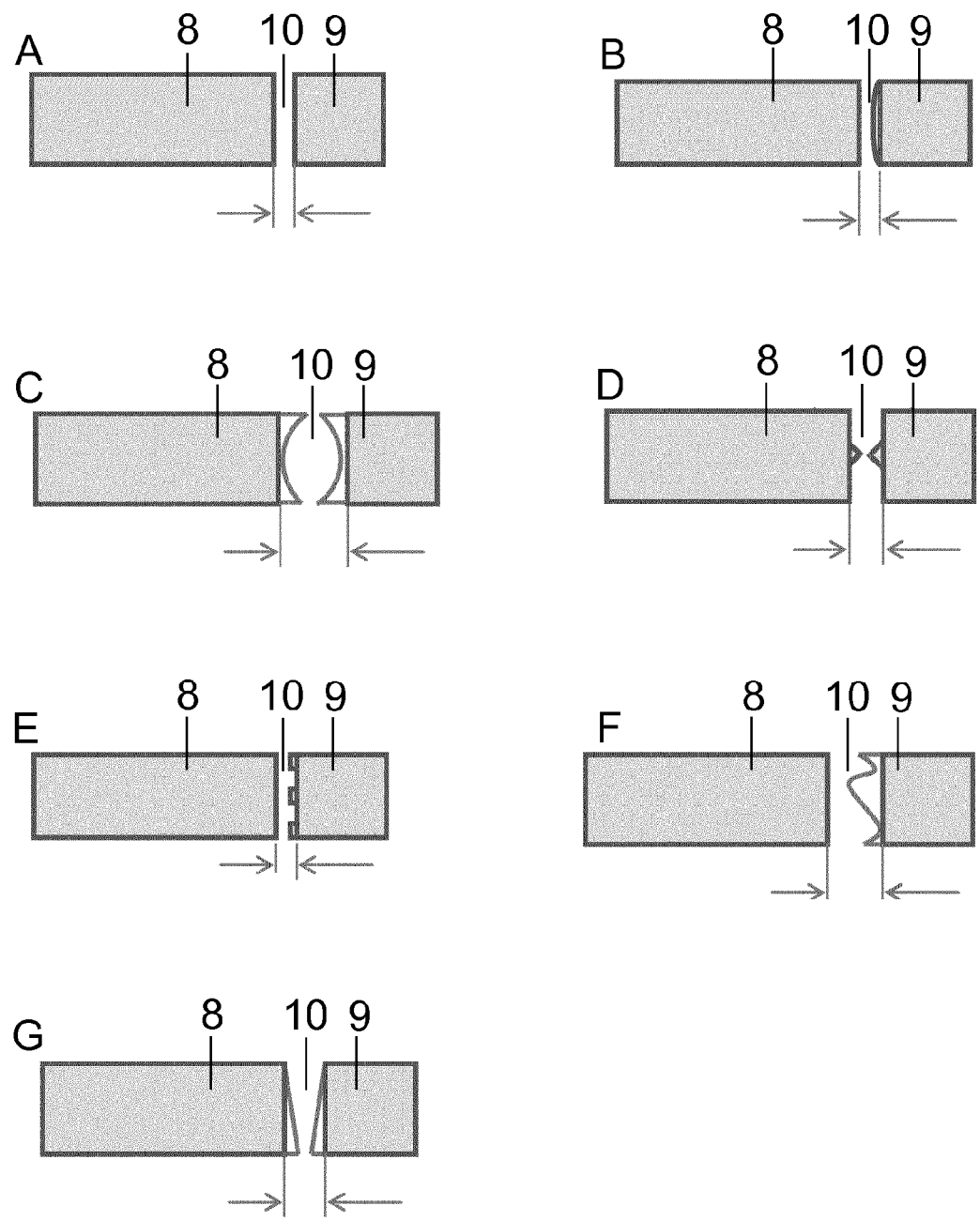
FIG. 6 A: Schematic drawing of two pieces (8, 9) separated by a planar seam (10) with uniform thickness. B-G: Schematic drawing of two tile pieces (8, 9) separated by a seam (10) with non-uniform thickness.

FIG. 6 shows an example of two tile pieces (8, 9) separated by a planar seam (10) with uniform thickness. Various examples of tile pieces (8, 9) separated by seam (10) with non-uniform thickness are further shown in FIGS. 6B-G. The seam with non-uniform thickness may be obtained if one or both neighboring surfaces of two adjacent tile pieces or tiles has a non-planar shape, for example as shown in FIG. 6 B, C, D, E and F. However, a seam with non-uniform thickness may also be obtained when both neighboring surfaces have a planar shape, as shown in FIG. 6 G. The non-uniform thickness of the seams may provide tailored strong and weak areas within the seams.

What is claimed is:

1. A method for manufacturing an endoprosthesis, the method comprising:
   providing a 3D model of a mold for the endoprosthesis
   meshing the 3D model, so as to divide the 3D model into two or more solid tile pieces with seams between the tile pieces;
   manufacturing a mold based on the meshed 3D model to form a manufactured mold, the manufactured mold comprising solid tile pieces with seams between said tile pieces;
   manufacturing an endoprosthesis using the manufactured mold; and
   mechanically separating the manufactured mold from the manufactured endoprosthesis by applying external mechanical force causing the manufactured mold to break along the seams.

2. The method of claim 1, further comprising incorporating onto the surface of the mold at least one structural feature not corresponding to at least part of the lumen anatomy of the patient for use in the manufacture of said endoprosthesis on the mold.

3. The method of claim 2, wherein the structural features comprise grooves, and wherein the grooves are configured to receive one or more wires for the endoprosthesis.

4. The method of claim 1, wherein the 3D model is based on a 3D image of at least part of a lumen anatomy of a patient.

5. The method of claim 1, wherein manufacturing the endoprosthesis using the manufactured mold further comprises laser cutting.

6. The method of claim 1, wherein manufacturing the endoprosthesis using the manufactured mold further comprises providing one or more wires for the endoprosthesis on the mold.

7. The method of claim 6, wherein manufacturing the endoprosthesis using the manufactured mold further comprises:
   wrapping a first wire in a helical manner around the manufactured mold;
   wrapping a second wire in a helical manner around the manufactured mold, wherein the second wire intersects one or more times with said first wire; and
   connecting the first wire and the second wire in one or more locations where the first wire and the second wire intersect.

8. The method of claim 6, wherein the wires comprise at least one of a shape memory alloy, super elastic alloy, polymer, and stainless steel.

9. The method of claim 1, wherein manufacturing the endoprosthesis using the manufactured mold further comprises providing a deploy mechanism for the endoprosthesis.

10. The method of claim 1, wherein the manufacturing further comprises manufacturing the mold using additive manufacturing.

11. The method of claim 10, wherein the additive manufacturing comprises at least one of stereolithography, selective laser sintering, selective laser melting, and fused deposition modeling.

12. The method of claim 1, wherein manufacturing the mold comprises utilizing a reduced amount of thermal energy for manufacturing the seams as compared to an amount of thermal energy utilized for manufacturing the solid tile pieces resulting in allowing for a reduced strength in the seams.

13. The method of claim 1, wherein the seams include less material per area than the two or more solid tile pieces which results in allowing for a reduced strength in the at least seams.

* * * * *